(12) United States Patent
Alsultan

(10) Patent No.: US 8,232,059 B2
(45) Date of Patent: Jul. 31, 2012

(54) **METHOD OF IDENTIFYING *A. BAUMANNII* WITH OXA-131-LIKE DRUG RESISTANCE IN DIABETIC PATIENTS**

(76) Inventor: Abdulrahman A. Alsultan, Alhafoof Wal Mubarraz (SA)

(*) Notice: Subject to any disclaimer, the term of this patent is extended or adjusted under 35 U.S.C. 154(b) by 165 days.

(21) Appl. No.: 12/801,546

(22) Filed: Jun. 14, 2010

(65) Prior Publication Data

US 2011/0306056 A1 Dec. 15, 2011

(51) Int. Cl.
*C12Q 1/68* (2006.01)
*C07H 21/02* (2006.01)
*C07H 21/04* (2006.01)

(52) U.S. Cl. ............ 435/6.15; 435/6.11; 435/6.18; 435/91.2; 436/94; 536/23.1; 536/23.7; 536/24.3

(58) Field of Classification Search .................. None
See application file for complete search history.

(56) References Cited

U.S. PATENT DOCUMENTS

| | | | |
|---|---|---|---|
| 5,811,242 | A | 9/1998 | Iwamoto et al. |
| 6,033,862 | A | 3/2000 | Matsuda et al. |
| 6,197,069 | B1 | 3/2001 | Poste et al. |
| 6,562,958 | B1 | 5/2003 | Breton et al. |
| 7,151,165 | B2 | 12/2006 | Venema et al. |
| 2007/0048751 | A1 | 3/2007 | Kim et al. |
| 2007/0128670 | A1 | 6/2007 | Klatzmann et al. |
| 2009/0075254 | A1 | 3/2009 | Ruano et al. |
| 2009/0123916 | A1 | 5/2009 | La Scola et al. |

FOREIGN PATENT DOCUMENTS

| | | |
|---|---|---|
| FR | 2909686 A1 | 6/2008 |
| JP | 10179140 A | 7/1998 |
| JP | 2000262281 A | 9/2000 |
| WO | WO 2009059379 A1 | 5/2009 |

OTHER PUBLICATIONS

Wang et al. Antimicrobial Agents and Chemotherapy. 2007. 51: 4022-4028.*

A.A. Alsultan, A. Hamouda, B.A. Evans, S.G.B. Amyes, *Acinetobacter baumannii*: Emergence of Four Strains with Novel bla$_{OXA-51-like}$ Genes in Patients with Diabetes Mellitus, *Journal of Chemotherapy*, vol. 21, No. 3 (290-295), 2009.

* cited by examiner

*Primary Examiner* — Carla Myers
(74) *Attorney, Agent, or Firm* — Richard C. Litman

(57) ABSTRACT

A method for identifying *A. baumannii* with OXA-131-like drug resistance in diabetic patients includes the steps of obtaining a sample from a patient; identifying an isolate as *A. baumannii*; screening the isolate for genes encoding an OXA-51-like enzyme; sequencing any of the genes encoding an OXA-51-like enzyme; and identifying the isolate as OXA-131-like when the sequence matches the sequence for OXA-90 (SEQ ID NO: 1), OXA-130 (SEQ ID NO: 2), OXA-131 (SEQ ID NO: 3), or OXA-132 (SEQ ID NO: 4). The method may further include the step of identifying the ISAba1 sequence upstream from the gene encoding the OXA-131-like enzyme.

2 Claims, No Drawings

SEQUENCE LISTING

<160> NUMBER OF SEQ ID NOS: 15

<210> SEQ ID NO 1
<211> LENGTH: 825
<212> TYPE: DNA
<213> ORGANISM: Acinetobacter baumannii

<400> SEQUENCE: 1

```
atgaacatta aagccctctt acttataaca agcgctattt ttatttcagc ctgctcacct      60
tatatagtga ctgctaatcc aaatcacagc gcttcaaaat ctgatgaaaa agcagagaaa     120
attaaaaatt tatttaacga agcacacact acgggtgttt tagttatcca acaaggccaa     180
actcaacaaa gctatggtaa tgatcttgct cgtgcttcga ccgagtatgt acctgcttcg     240
accttcaaaa tgcttaatgc tttgatcggc cttgagcacc ataaggcaac caccacagaa     300
gtatttaagt gggatggtaa aaaaaggtta ttcccagaat gggaaaagga catgacccta     360
ggcgatgcca tgaaagcttc cgctattcca gtttatcaag atttagctcg tcgtattgga     420
cttgagctca tgtctaagga agtgaagcgt gttggttatg gcaatgcaga tatcggtacc     480
caagtcgata atttttggct agtgggtcct ttaaaaatta ctcctcagca agaggcacag     540
tttgcttaca agctagctaa taaaacgctt ccatttagcc aaaaagtcca agatgaagtg     600
caatccatgc tattcataga agaaaagaat ggaaacaaaa tatacgcaaa aagtggttgg     660
ggatgggatg tagacccaca agtaggctgg ttaactggat gggttgttca gcctcaagga     720
aatattgtag cgttctccct taacttagaa atgaaaaaag gaatacctag ctctgttcga     780
aaagagatta cttataaaag tttagaacaa ttaggtattt tatag                    825
```

<210> SEQ ID NO 2
<211> LENGTH: 825
<212> TYPE: DNA
<213> ORGANISM: Acinetobacter baumannii

<400> SEQUENCE: 2

```
atgaacatta aagcactctt acttataaca agcgctattt ttatttcagc ctgctcacct      60
tatatagtga ctactaatcc aaatcacagc gcttcaaaat ctgatgaaaa agcagagaaa     120
attaaaaatt tatttaacga agcacacact acgggtgttt tagttatcca acaaggccaa     180
actcaacaaa gctatggtaa tgatcttgct cgtgcttcga ccgagtatgt acctgcttcg     240
accttcaaaa tgcttaatgc tttgatcggc cttgagcacc ataaggcaac caccacagaa     300
gtatttaagt gggatggtaa aaaaaggtta ttcccagaat gggaaaagga catgaccccta    360
```

```
ggcgatgcca tgaaagcttc cgctattcca gtttatcaag atttagctcg tcgtattgga    420
cttgagctca tgtctaagga agtgaagcgt gttggttatg gcaatacaga tatcggtacc    480
caagtcgata attttttggct ggtgggtcct ttaaaaatta ctcctcagca agaggcacag    540
tttgcttaca agctagctaa taaaacgctt ccatttagcc aaaaagtcca agatgaagtg    600
caatccatgc tattcataga agaaagaat ggaaataaaa tatacgcaaa aagtggttgg    660
ggatgggatg tagacccaca agtaggctgg ttaactggat gggttgttca gcctcaaggg    720
aatattgtag cgttctccct taacttagaa atgaaaaaag gaatacctag ctctgttcga    780
aaagagatta cttataaaag tttagaacaa ttaggtattt tatag                    825
```

```
<210> SEQ ID NO 3
<211> LENGTH: 825
<212> TYPE: DNA
<213> ORGANISM: Acinetobacter baumannii

<400> SEQUENCE: 3
atgaacatta aagcactctt acttataaca agcgctattt ttatttcagc ctgctcacct    60
tatatagtga ctgctaatcc aaatcacagc gcttcaaaat ctgatgtaaa agcagagaaa   120
attaaaaatt tatttaacga agcacacact acgggtgttt tagttatcca acaaggccaa   180
actcaacaaa gctatggtaa tgatcttgct cgtgcttcga ccgagtatgt acctgcttcg   240
accttcaaaa tgcttaatgc tttgatcggc cttgagcacc ataaggcaac caccacagaa   300
gtatttaagt gggatggtaa aaaaaggtta ttcccagaat gggaaaagga catgacccta   360
ggcgatgcca tgaaagcttc cgctgttcca gtttatcaag atttagctcg tcgtattgga   420
cttgagctca tgtctaagga agtgaagcgt gttggttatg gcaatgcaga tatcggtacc   480
caagtcgata attttttggct ggtgggtcct ttaaaaatta ctcctcagca agaggcacag   540
tttgcttaca agctagctaa taaaacgctt ccatttagcc aaaaagtcca agatgaagtg   600
caatccatgc tattcataga agaaagaat ggaaacaaaa tatacgcaaa aagtggttgg   660
ggatgggatg taaaccaaca agtaggctgg ttaactggat gggttgttca gcctcaaggg   720
aatattgtag cgttctccct taacttagaa atgaaaaaag gaatacctag ctctgttcga   780
aaagagatta cttataaaag cttagaacaa ttaggtattt tatag                    825
```

```
<210> SEQ ID NO 4
<211> LENGTH: 825
<212> TYPE: DNA
<213> ORGANISM: Acinetobacter baumannii

<400> SEQUENCE: 4
atgaacatta aaacactctt acttataaca agcgctattt ttatttcagc ctgctcacct    60
tatatagtga ctgctaatcc aaatcacagc gcttcaaaat ctgatgaaaa agcagagaaa   120
attaaaaatt tatttaacga agtacacact acgggtgttt tagttatcca acaaggccaa   180
actcaacaaa gctatggtaa tgatcttgct cgtgcttcga ccgagtatgt acctgcttcg   240
accttcaaaa tgcttaatgc tttgatcggc cttgagcacc ataaggcaac caccacagaa   300
gtatttaagt gggacgggca aaaaaggcta ttcccagaat gggaaaagga catgacccta   360
ggcgatgcta tgaaagcttc cgctattccg gtttatcaag atttagctcg tcgtattgga   420
cttgaactca tgtctaagga agtgaagcgt gttggttatg gcaatgcaga tatcggtacc   480
caagtcgata attttttggct ggtgggtcct ttaaaaatta ctcctcagca agaggcacag   540
tttgcttaca agctagctaa taaaacgctt ccatttagcc caaaagtcca agatgaagtg   600
```

```
caatccatgt tattcataga agaaaagaat ggaaataaaa tatacgcaaa aagtggttgg    660
ggatgggatg tagacccaca agtaggctgg ttaactggat gggttgttca gcctcaagga    720
aatattgtag cgttctccct taacttagaa atgaaaaaag gaataccbag ctctgttcga    780
aaagagatga cttataaaag tttagaacaa ttaggtattt tatag                   825
```

<210> SEQ ID NO 5
<211> LENGTH: 274
<212> TYPE: PRT
<213> ORGANISM: Acinetobacter baumannii

<400> SEQUENCE: 5

```
Met Asn Ile Lys Ala Leu Leu Ile Thr Ser Ala Ile Phe Ile Ser
1               5                   10                  15

Ala Cys Ser Pro Tyr Ile Val Thr Ala Asn Pro Asn His Ser Ala Ser
            20                  25                  30

Lys Ser Asp Glu Lys Ala Glu Lys Ile Lys Asn Leu Phe Asn Glu Ala
        35                  40                  45

His Thr Thr Gly Val Leu Val Ile Gln Gln Gly Gln Thr Gln Gln Ser
    50                  55                  60

Tyr Gly Asn Asp Leu Ala Arg Ala Ser Thr Glu Tyr Val Pro Ala Ser
65                  70                  75                  80

Thr Phe Lys Met Leu Asn Ala Leu Ile Gly Leu Glu His His Lys Ala
                85                  90                  95

Thr Thr Thr Glu Val Phe Lys Trp Asp Gly Lys Lys Arg Leu Phe Pro
            100                 105                 110

Glu Trp Glu Lys Asp Met Thr Leu Gly Asp Ala Met Lys Ala Ser Ala
        115                 120                 125

Ile Pro Val Tyr Gln Asp Leu Ala Arg Arg Ile Gly Leu Glu Leu Met
    130                 135                 140

Ser Lys Glu Val Lys Arg Val Gly Tyr Gly Asn Ala Asp Ile Gly Thr
145                 150                 155                 160

Gln Val Asp Asn Phe Trp Leu Val Gly Pro Leu Lys Ile Thr Pro Gln
                165                 170                 175

Gln Glu Ala Gln Phe Ala Tyr Lys Leu Ala Asn Lys Thr Leu Pro Phe
            180                 185                 190

Ser Gln Lys Val Gln Asp Glu Val Gln Ser Met Leu Phe Ile Glu Glu
        195                 200                 205

Lys Asn Gly Asn Lys Ile Tyr Ala Lys Ser Gly Trp Gly Trp Asp Val
    210                 215                 220

Asp Pro Gln Val Gly Trp Leu Thr Gly Trp Val Val Gln Pro Gln Gly
225                 230                 235                 240

Asn Ile Val Ala Phe Ser Leu Asn Leu Glu Met Lys Lys Gly Ile Pro
                245                 250                 255

Ser Ser Val Arg Lys Glu Ile Thr Tyr Lys Ser Leu Glu Gln Leu Gly
            260                 265                 270

Ile Leu
```

<210> SEQ ID NO 6
<211> LENGTH: 274
<212> TYPE: PRT
<213> ORGANISM: Acinetobacter baumannii

<400> SEQUENCE: 6

```
Met Asn Ile Lys Ala Leu Leu Ile Thr Ser Ala Ile Phe Ile Ser
1               5                   10                  15
```

```
Ala Cys Ser Pro Tyr Ile Val Thr Thr Asn Pro Asn His Ser Ala Ser
             20                  25                  30

Lys Ser Asp Glu Lys Ala Glu Lys Ile Lys Asn Leu Phe Asn Glu Ala
         35                  40                  45

His Thr Thr Gly Val Leu Val Ile Gln Gln Gly Gln Thr Gln Gln Ser
     50                  55                  60

Tyr Gly Asn Asp Leu Ala Arg Ala Ser Thr Glu Tyr Val Pro Ala Ser
 65                  70                  75                  80

Thr Phe Lys Met Leu Asn Ala Leu Ile Gly Leu Glu His His Lys Ala
                 85                  90                  95

Thr Thr Thr Glu Val Phe Lys Trp Asp Gly Lys Lys Arg Leu Phe Pro
            100                 105                 110

Glu Trp Glu Lys Asp Met Thr Leu Gly Asp Ala Met Lys Ala Ser Ala
        115                 120                 125

Ile Pro Val Tyr Gln Asp Leu Ala Arg Arg Ile Gly Leu Glu Leu Met
    130                 135                 140

Ser Lys Glu Val Lys Arg Val Gly Tyr Gly Asn Thr Asp Ile Gly Thr
145                 150                 155                 160

Gln Val Asp Asn Phe Trp Leu Val Gly Pro Leu Lys Ile Thr Pro Gln
                165                 170                 175

Gln Glu Ala Gln Phe Ala Tyr Lys Leu Ala Asn Lys Thr Leu Pro Phe
            180                 185                 190

Ser Gln Lys Val Gln Asp Glu Val Gln Ser Met Leu Phe Ile Glu Glu
        195                 200                 205

Lys Asn Gly Asn Lys Ile Tyr Ala Lys Ser Gly Trp Gly Trp Asp Val
    210                 215                 220

Asp Pro Gln Val Gly Trp Leu Thr Gly Trp Val Val Gln Pro Gln Gly
225                 230                 235                 240

Asn Ile Val Ala Phe Ser Leu Asn Leu Glu Met Lys Lys Gly Ile Pro
                245                 250                 255

Ser Ser Val Arg Lys Glu Ile Thr Tyr Lys Ser Leu Glu Gln Leu Gly
            260                 265                 270

Ile Leu

<210> SEQ ID NO 7
<211> LENGTH: 274
<212> TYPE: PRT
<213> ORGANISM: Acinetobacter baumannii

<400> SEQUENCE: 7

Met Asn Ile Lys Ala Leu Leu Leu Ile Thr Ser Ala Ile Phe Ile Ser
 1               5                  10                  15

Ala Cys Ser Pro Tyr Ile Val Thr Ala Asn Pro Asn His Ser Ala Ser
             20                  25                  30

Lys Ser Asp Val Lys Ala Glu Lys Ile Lys Asn Leu Phe Asn Glu Ala
         35                  40                  45

His Thr Thr Gly Val Leu Val Ile Gln Gln Gly Gln Thr Gln Gln Ser
     50                  55                  60

Tyr Gly Asn Asp Leu Ala Arg Ala Ser Thr Glu Tyr Val Pro Ala Ser
 65                  70                  75                  80

Thr Phe Lys Met Leu Asn Ala Leu Ile Gly Leu Glu His His Lys Ala
                 85                  90                  95

Thr Thr Thr Glu Val Phe Lys Trp Asp Gly Lys Lys Arg Leu Phe Pro
            100                 105                 110
```

```
Glu Trp Glu Lys Asp Met Thr Leu Gly Asp Ala Met Lys Ala Ser Ala
            115                 120                 125

Val Pro Val Tyr Gln Asp Leu Ala Arg Arg Ile Gly Leu Glu Leu Met
130                 135                 140

Ser Lys Glu Val Lys Arg Val Gly Tyr Gly Asn Ala Asp Ile Gly Thr
145                 150                 155                 160

Gln Val Asp Asn Phe Trp Leu Val Gly Pro Leu Lys Ile Thr Pro Gln
                165                 170                 175

Gln Glu Ala Gln Phe Ala Tyr Lys Leu Ala Asn Lys Thr Leu Pro Phe
            180                 185                 190

Ser Gln Lys Val Gln Asp Glu Val Gln Ser Met Leu Phe Ile Glu Glu
            195                 200                 205

Lys Asn Gly Asn Lys Ile Tyr Ala Lys Ser Gly Trp Gly Trp Asp Val
            210                 215                 220

Asn Gln Gln Val Gly Trp Leu Thr Gly Trp Val Val Gln Pro Gln Gly
225                 230                 235                 240

Asn Ile Val Ala Phe Ser Leu Asn Leu Glu Met Lys Lys Gly Ile Pro
                245                 250                 255

Ser Ser Val Arg Lys Glu Ile Thr Tyr Lys Ser Leu Glu Gln Leu Gly
            260                 265                 270

Ile Leu

<210> SEQ ID NO 8
<211> LENGTH: 274
<212> TYPE: PRT
<213> ORGANISM: Acinetobacter baumannii

<400> SEQUENCE: 8

Met Asn Ile Lys Thr Leu Leu Leu Ile Thr Ser Ala Ile Phe Ile Ser
1               5                   10                  15

Ala Cys Ser Pro Tyr Ile Val Thr Ala Asn Pro Asn His Ser Ala Ser
            20                  25                  30

Lys Ser Asp Glu Lys Ala Glu Lys Ile Lys Asn Leu Phe Asn Glu Val
        35                  40                  45

His Thr Thr Gly Val Leu Val Ile Gln Gln Gly Gln Thr Gln Gln Ser
    50                  55                  60

Tyr Gly Asn Asp Leu Ala Arg Ala Ser Thr Glu Tyr Val Pro Ala Ser
65                  70                  75                  80

Thr Phe Lys Met Leu Asn Ala Leu Ile Gly Leu Glu His His Lys Ala
                85                  90                  95

Thr Thr Thr Glu Val Phe Lys Trp Asp Gly Gln Lys Arg Leu Phe Pro
            100                 105                 110

Glu Trp Glu Lys Asp Met Thr Leu Gly Asp Ala Met Lys Ala Ser Ala
            115                 120                 125

Ile Pro Val Tyr Gln Asp Leu Ala Arg Arg Ile Gly Leu Glu Leu Met
130                 135                 140

Ser Lys Glu Val Lys Arg Val Gly Tyr Gly Asn Ala Asp Ile Gly Thr
145                 150                 155                 160

Gln Val Asp Asn Phe Trp Leu Val Gly Pro Leu Lys Ile Thr Pro Gln
                165                 170                 175

Gln Glu Ala Gln Phe Ala Tyr Lys Leu Ala Asn Lys Thr Leu Pro Phe
            180                 185                 190

Ser Pro Lys Val Gln Asp Glu Val Gln Ser Met Leu Phe Ile Glu Glu
            195                 200                 205

Lys Asn Gly Asn Lys Ile Tyr Ala Lys Ser Gly Trp Gly Trp Asp Val
```

```
            210                 215                 220
Asp Pro Gln Val Gly Trp Leu Thr Gly Trp Val Val Gln Pro Gln Gly
225                 230                 235                 240

Asn Ile Val Ala Phe Ser Leu Asn Leu Glu Met Lys Lys Gly Ile Pro
                245                 250                 255

Ser Ser Val Arg Lys Glu Met Thr Tyr Lys Ser Leu Glu Gln Leu Gly
            260                 265                 270

Ile Leu

<210> SEQ ID NO 9
<211> LENGTH: 19
<212> TYPE: DNA
<213> ORGANISM: Acinetobacter baumannii

<400> SEQUENCE: 9
ttgtacacac cgcccgtca                                          19

<210> SEQ ID NO 10
<211> LENGTH: 21
<212> TYPE: DNA
<213> ORGANISM: Acinetobacter baumannii

<400> SEQUENCE: 10
ggtacttaga tgtttcagtt c                                       21

<210> SEQ ID NO 11
<211> LENGTH: 20
<212> TYPE: DNA
<213> ORGANISM: Acinetobacter baumannii

<400> SEQUENCE: 11
taatgctttg atcggccttg                                         20

<210> SEQ ID NO 12
<211> LENGTH: 20
<212> TYPE: DNA
<213> ORGANISM: Acinetobacter baumannii

<400> SEQUENCE: 12
tggattgcac ttcatcttgg                                         20

<210> SEQ ID NO 13
<211> LENGTH: 21
<212> TYPE: DNA
<213> ORGANISM: Acinetobacter baumannii

<400> SEQUENCE: 13
ctaataattg atctactcaa g                                       21

<210> SEQ ID NO 14
<211> LENGTH: 25
<212> TYPE: DNA
<213> ORGANISM: Acinetobacter baumannii

<400> SEQUENCE: 14
ccagtggatg gatggataga ttatc                                   25

<210> SEQ ID NO 15
<211> LENGTH: 20
<212> TYPE: DNA
<213> ORGANISM: Acinetobacter baumannii
```

```
<400> SEQUENCE: 15
gacctgcaaa gaagcgctgc                                                  20
```

METHOD OF IDENTIFYING *A. BAUMANNII* WITH OXA-131-LIKE DRUG RESISTANCE IN DIABETIC PATIENTS

INCORPORATION BY REFERENCE OF MATERIAL SUBMITTED IN COMPUTER READABLE FORM

The Applicant hereby incorporate by reference the sequence listing contained in the ASCII text file titled 32087_00_rev_sequence_ST25.txt, created Apr. 24, 2012 and having 15.3 KB of data (16.0 KB on disk).

BACKGROUND OF THE INVENTION

1. Field of the Invention

The present invention relates to methods of identifying drug-resistant bacteria, and particularly to a method of identifying *A. baumannii* with OXA-131-like drug resistance in diabetic patients.

2. Description of the Related Art

*Acinetobacter baumannii* is an aerobic gram-negative species of bacteria that is resistant to most antibiotics. Infection by *A. baumannii* can result in pneumonia and infections of the urinary tract, the bloodstream, and other parts of the body. Left untreated, such infections can result in extended and debilitating convalescence, and may prove fatal. *A. baumannii* infects those with compromised immune systems, such as the wounded, the elderly, children, those with debilitating diseases, such as diabetes or other diseases or illnesses that might weaken the immune system. *A. baumannii* has been implicated as the source of nocosomial infections in hospitals and other treatment facilities, with the number of reported nocosomial infections linked to *A. baumannii* increasing in number in recent years.

The treatment of choice has traditionally been carbapenems (the carbapenems include meropenem, ertapenem, imipenem, doripenem, panapenem, and biapenem), since *A. baumannii* is resistant to many other antibiotics. The carbapenems are a class of beta-lactam antibiotics effective against a broad spectrum of bacterial infection and resistance to β-lactamases.

In recent years, however, many strains of *A. baumannii* have shown resistance to the carbapenems. Such resistance results from genes encoding carbapenemases, which have most commonly either been molecular class B metallo-β-lactamases, or molecular class D OXA β-lactamases (so-named for resistance to oxacillin and related compounds). The OXA β-lactamases exhibiting resistance to carbapenems have generally fallen into one of four subgroups: OXA-23-like, OXA-24-like, OXA-58-like, and OXA-51-like. The $bla_{OXA-51-like}$ gene is found in all strains of *A. baumannii*, and may be used as a marker for identifying *A. baumannii*. The OXA-51-like subgroup generally exhibits a low level of carbapenem resistance, but when the ISAba1 sequence is upstream of the gene encoding the enzyme, the OXA-51-like enzyme is overexpressed and the gene is more likely to replicate. It is thought that the ISAba1 sequence may act as a promoter when it is upstream from the gene encoding the OXA-51-like enzyme, signaling the start of the gene for messenger RNA to transcribe when expressing the enzyme. As used herein, the term "OXA-51-like" refers to a subgroup of OXA enzymes that includes a group of enzymes with OXA numbers 51, 64, 65, 66, 67, 68, 69, 70, 71, 75, 76, 77, 83, 84, 86, 87, 88, 89, 91, 92, 94 and 95. OXA enzymes may or may not have similar structure, and many of the genes encoding the enzymes may have no more than 20% homology in their sequence. β-lactamases are thought to confer drug resistance to carbapenemases by hydrolysing (or hydrolyzing) and opening the β-lactam ring, rendering the carbapenem ineffectual.

The present inventor has identified four new strains of *A. baumannii* with novel $bla_{OXA-51-like}$ genes, which encode four enzymes that the inventor refers to as OXA-131-like, the OXA-131 subgroup including OXA-90 (SEQ ID NO: 5), OXA-130 (SEQ ID NO: 6), OXA-131 (SEQ ID NO: 7), and OXA-132 (SEQ ID NO: 8). The OXA-90 gene has the sequence of nucleotides shown in SEQ ID NO: 1 in the attached Sequence Listing. The OXA-130 gene has the sequence of nucleotides shown in SEQ ID NO: 2 in the attached Sequence Listing. The OXA-131 gene has the sequence of nucleotides shown in SEQ ID NO: 3 in the attached Sequence Listing. The OXA-132 gene has the sequence of nucleotides shown in SEQ ID NO: 4 in the attached Sequence Listing.

Each enzyme encodes a β-lactamase that exhibits some degree of carbapenemase activity, and is also resistant to several other antibiotics. Because Infection by *A. baumannii* may lead to prolonged convalescence or may prove fatal, it is desirable is identify the strain of *A. baumannii* quickly in order to make an informed selection of an antibiotic for treatment of the infection.

Thus, a method of identifying *A. baumannii* with OXA-131-like drug resistance in diabetic patients solving the aforementioned problems is desired.

SUMMARY OF THE INVENTION

A method for identifying *A. baumannii* with OXA-131-like drug resistance in diabetic patients includes the steps of obtaining a sample from a patient; identifying an isolate as *A. baumannii*; screening the isolate for genes encoding an OXA-51-like enzyme; sequencing any of the genes encoding an OXA-51-like enzyme; and identifying the isolate as OXA-131-like when the sequence matches the sequence for OXA-90 (SEQ ID NO: 1), OXA-130 (SEQ ID NO: 2), OXA-131 (SEQ ID NO: 3), or OXA-132 (SEQ ID NO: 4). The method may further include the step of identifying the ISAba1 sequence upstream from the gene encoding the OXA-131-like enzyme.

These and other features of the present invention will become readily apparent upon further review of the following specification.

DETAILED DESCRIPTION OF THE PREFERRED EMBODIMENTS

A method for identifying *A. baumannii* with OXA-131-like drug resistance in diabetic patients includes the steps of obtaining a sample from a patient; identifying an isolate as *A. baumannii*; screening the isolate for genes encoding an OXA-51-like enzyme; sequencing any of the genes encoding an OXA-51-like enzyme; and identifying the isolate as OXA-131-like when the sequence matches the sequence for OXA-90 (SEQ ID NO: 1), OXA-130 (SEQ ID NO: 2), OXA-131 (SEQ ID NO: 3), or OXA-132 (SEQ ID NO: 4). The method may further include the step of identifying the ISAba1 sequence upstream from the gene encoding the OXA-131-like enzyme.

In addition to the nucleotide sequences in the attached Sequence Listing, the amino acid sequences for each enzyme are also provided. The OXA-90 enzyme has the sequence of amino acids shown in SEQ ID NO: 5 in the attached Sequence Listing (i.e., SEQ ID NO: 1 is a nucleotide sequence of a portion of a gene encoding the OXA-90 enzyme, which has the amino acid sequence of SEQ ID NO: 5; the enzyme may be expressed under certain circumstances, notably when the ISAba1 sequence is upstream from SEQ ID NO: 1). The OXA-130 enzyme has the sequence of amino acids shown in SEQ ID NO: 6 in the attached Sequence Listing. The OXA-131 enzyme has the sequence of amino acids shown in SEQ ID NO: 7 in the attached Sequence Listing. The OXA-132 enzyme has the sequence of amino acids shown in SEQ ID NO: 8 in the attached Sequence Listing.

As described in the article A. A. Alsultan, A. Hamouda, B. A. Evans, S. G. B. Amyes, "*Acinetobacter baumannii*. Emergence of Four Strains with Novel bla$_{OXA-51-like}$ Genes in Patients with Diabetes Mellitus", *Journal of Chemotherapy*, Vol. 21, No. 3 (290-295), 2009, which is hereby incorporated by reference in its entirety, the present inventor identified the four new strains of *A. baumannii* with OXA-131-like drug resistance as a result of a study of clinical samples obtained from diabetic patients at four hospitals and twenty medical centers in Saudi Arabia. All of the patients had diabetes mellitus and suffered from deep-sited infections.

Twenty isolates were identified phenotypically as *A. calcoceticus/A. baumannii* complex by API 20 NE (BioMerieux, Marcy L'Etoile, France). The isolates were further identified to the genomic level by restrictive polymorphism in the 16S-23S rRNA intragenic region. DNA from each strain was obtained by emulsifying a single colony from overnight growth, sequences of primer 1 (5'-TTG TAC ACA CCG CCC GTC A-'3) (SEQ ID NO: 9) and primer 2 (5'-GGT ACT TAG ATG TTT CAG TTC-'3) (SEQ ID NO: 10) were used to amplify a 975 bp section of the gene using PCR, and the amplification products were analyzed by gel electrophoresis.

The twenty isolates were screened for genes encoding OXA-51-like enzymes using multiplex PCR, with the primer pairs (5'-TAA TGC TTT GAT CGG CCT TG-'3) (SEQ ID NO: 11) and (5'-TGG ATT GCA CTT CAT CTT GG-'3) (SEQ ID NO: 12) being used to amplify a 353 bp segment of the bla$_{OXA-51-like}$ gene. PCR amplifications were also performed with the primers OXA69A (5'-CTA ATA ATT GAT CTA CTC AAG-'3) (SEQ ID NO: 13) and OXA-69B (5'-CCA GTG GAT GGA TGG ATA GAT TAT C-'3) (SEQ ID NO: 14) to obtain a 975 bp segment that contained the coding sequence of the entire bla$_{OXA-51-like}$ gene. Isolates producing a band of more than about 2000 bp resulting from an insertion upstream of the bla$_{OXA-51-like}$ gene were re-analyzed by using the primers preABprom+ (5'-GAC CTG CAA AGA AGC GCT GC-'3) (SEQ ID NO: 15) to generate an 1189 bp product, which was then sequenced.

All isolates were typed by pulsed field gel electrophoresis (PGFE). All isolates were analyzed by BioNumerics software version 4.

Of the twenty isolates, nine strains contained four novel OXA-51-like enzymes [four with genes encoding OXA-131 (SEQ ID NO: 3), one with a gene encoding OXA-130 (SEQ ID NO: 2), two with genes encoding OXA-90 (SEQ ID NO: 1), and two with genes encoding OXA-132 (SEQ ID NO: 4)], the remaining isolates containing other previously known OXA-enzymes. Of the four newly identified OXA-51-like enzymes, only the gene encoding the OXA-131 enzyme (SEQ ID NO: 3) also was found with the ISAba1 sequence upstream from the gene encoding the OXA-enzyme.

All twenty isolates were further tested for MICs (minimum inhibitory concentrations) for susceptibility to several known antibiotics using the British Society for Antimicrobial Chemotherapy guidelines. The results are summarized in Table I. It will be seen that all twenty isolates were highly resistant to ertapenem, oxacillin, ampicillin, sulbactam, chloramphenicol, and tetracycline. The majority was also resistant to ciprofloxacin, gentamicin, piperacillin/tazobactam, amoxacillin/clavulanate, nalidixic acid, rifampicin, and ofloxacin. All isolates were susceptible to imipenem and colistin, and all but four isolates (which had low-level resistance) were susceptible to meropenem.

TABLE I

Antimicrobial susceptibility in 20 isolates

| Antibiotic | No. of resistant isolates | MIC range (mg/L) | % resistance |
|---|---|---|---|
| Imipenem | 0 | 0.25-2 | 0 |
| Meropenem | 4 | 4-8 | 20 |
| Ertapenem | 20 | 4-64 | 100 |
| Ciprofloxacin | 9 | 1-16 | 45 |
| Gentamicin | 4 | 32->128 | 20 |
| Oxacillin | 20 | >128 | 100 |
| Pipericillin/tazobactam | 11 | 32-128 | 55 |
| Ampicillin | 20 | 16->128 | 100 |
| Amoxicillin/clavulanate | 18 | 16->128 | 90 |
| Nalidixic Acid | 15 | 8->128 | 75 |
| Colistin | 0 | 0.25-0.5 | 0 |
| Rifampicin | 16 | 4-32 | 80 |
| Sulbactam | 20 | 64->128 | 100 |
| Ofloxacin | 14 | 1-32 | 70 |
| Chloramphenicol | 20 | >128 | 100 |
| Tetracycline | 20 | 2->128 | 100 |

It will be noted that all samples were from diabetic patients. However, the four OXA-131-like enzymes have not been previously identified in *Acinetobacter baumannii* isolates obtained from the general population. This suggests that these four new strains of *Acinetobacter baumannii* may evidence the emergence of drug-resistant *Acinetobacter baumannii* strains that pose a threat unique to the diabetic patient.

Diabetic patients are ten times more likely to develop *Acinetobacter baumannii* infections than the remainder of the population. Carbapenems are one of the very few antibiotics that effectively treat infections caused by this organism. Carbapenem-resistant strains of *Acinetobacter* baumannii can cause serious complications in diabetic patients.

The above identifies a new risk factor in diabetics. Emergence of new strains of *A. baumannii* isolated from patients with diabetes mellitus could reach epidemic levels. The percentage of *A. baumannii* isolates from those patients having strains with OXA-51-like β-lactamases was found to be high (approximately 45%). OXA-51-like β-lactamases are found to significantly contribute to carbapenem resistance, and this resistance correlates both with the survival of *A. baumannii* in diabetics and perhaps also in the development of diabetes.

There are certain gene variants that predispose people to develop diabetes, and these variations play a significant role in the development of a large spectrum of effects, which may include infections with *A. baumannii*. Nine representative isolates of *A. baumannii* from patients with diabetes mellitus were found to possess common gene variants encoding β-lactamases designated as OXA-90 (SEQ ID NO: 1), OXA-130 (SEQ ID NO: 2), OXA-131 (SEQ ID NO: 3), and OXA-132 (SEQ ID NO: 4). Previously, all variations in amino acids in OXA-51-like enzymes were found to be outside of class D carbapenemase motifs, which is consistent with the four enzymes identified in the above study.

The isolates with a polymerase chain reaction (PCR) product larger than c. 2000 bp using the primers OXA-69A and OXA-69B produced an 1189 bp product with the second set of primers. The nucleotide sequences of these strains had the insertion sequence ISAba1 located seven base pairs upstream from the open reading frame of the bla$_{OXA-131}$ gene, which was the most frequent bla$_{OXA\text{-}51\text{-}like}$ gene (approximately 44%), compared to bla$_{OXA\text{-}130}$ (approximately 11%), bla$_{OXA\text{-}132}$ (approximately 22%), and bla$_{OXA\text{-}90}$ (approximately 22%). Insertion of the sequence ISAba1 is widespread in *A. baumannii* with more than 13 copies in one cell and, through mobilization, can act as a "moving switch" to upregulate expression of downstream genes. The presence of ISAba1 upstream of bla$_{OXA\text{-}131\text{-}like}$ indicates that it has a significant role in both the transmission and expression of these genes to diabetic patients.

The study suggests that carbapenem resistance in *A. baumannii* may emerge in diabetics in regions that have, up to now, managed to avoid the problem. The dissemination of the strains of *A. baumannii* carrying the OXA-131 β-lactamase, with the insertion sequence ISAba1 upstream of the encoding gene, appears to threaten diabetics and may increase the risk due to the upregulation of bla$_{OXA\text{-}131}$ gene expression.

Thus, in order to predict complications in patients with diabetes mellitus, the patients are tested for the existence of *A. baumannii* harboring the bla$_{OXA\text{-}131}$ gene, with the insertion sequence ISAba1 being found upstream of the encoding gene. Testing whether a patient has *A. baumannii* harboring the bla$_{OXA\text{-}131}$ gene with the insertion sequence ISAba1 upstream of the encoding gene may be an essential step in monitoring their carbapenem resistance phenotype and may assist in preventing their spread in diabetics, as well as allowing time for the individual patient to receive preventive care before the emergence of infectious symptoms.

It is to be understood that the present invention is not limited to the embodiment described above, but encompasses any and all embodiments within the scope of the following claims.

I claim:

1. A method for identifying an isolate as a member of a subgroup of *A. baumannii* with antibiotic drug resistance, comprising the steps of:
   a) obtaining a sample from a patient;
   b) identifying an isolate from the sample as *A. baumannii*;
   c) screening the isolate for genes encoding an OXA-51-like enzyme;
   d) sequencing any genes encoding an OXA-51-like enzyme; and
   e) identifying the isolate as a member of the subgroup of *A. baumannii* having antibiotic drug resistance when the sequence of the gene encoding an OXA-51-like enzyme determined in d) is OXA-90 (SEQ ID NO: 1), OXA-130 (SEQ ID NO: 2), OXA-131 (SEQ ID NO: 3), or OXA-132 (SEQ ID NO: 4).

2. The method for identifying a subgroup of *A. baumannii* with antibiotic drug resistance as recited in claim 1, further comprising the step of identifying the ISAba1 sequence upstream from the gene encoding the enzyme of the member of the subgroup having antibiotic drug resistance, thereby confirming drug resistance due to the enzyme.

* * * * *